United States Patent [19]

Rasmussen et al.

[11] Patent Number: 5,236,838
[45] Date of Patent: Aug. 17, 1993

[54] ENZYMATICALLY ACTIVE RECOMBINANT GLUCOCEREBROSIDASE

[75] Inventors: James Rasmussen, Boston; Gary Barsomian, Georgetown; Michel Bergh, Belmont, all of Mass.

[73] Assignee: Genzyme Corporation, Cambridge, Mass.

[21] Appl. No.: 748,283

[22] Filed: Aug. 21, 1991

Related U.S. Application Data

[60] Division of Ser. No. 455,507, Dec. 22, 1989, abandoned, which is a continuation-in-part of Ser. No. 289,589, Dec. 23, 1988, abandoned.

[51] Int. Cl.⁵ .................. C12N 9/42; C12N 15/56; C12N 15/85
[52] U.S. Cl. .................................. 435/209; 435/69.1; 435/69.8; 435/70.3; 435/70.1; 435/172.3; 435/240.2; 435/320.1; 536/23.2; 935/14; 935/27; 935/34; 935/50; 935/70; 935/66
[58] Field of Search .................... 435/69.1, 69.8, 70.1, 435/70.3, 172.3, 200, 209, 240.2, 320.1; 800/2, DIG. 2; 935/22, 23, 27, 32, 50, 70; 536/23.2

[56] References Cited

U.S. PATENT DOCUMENTS

| | | | |
|---|---|---|---|
| 4,675,285 | 6/1987 | Clark et al. | 435/6 |
| 4,713,339 | 12/1987 | Levinson et al. | 435/240.2 |
| 4,727,138 | 2/1988 | Goeddel et al. | 536/27 |

OTHER PUBLICATIONS

Martin, B. et al. "Glycosylation and Processing of High Levels of Active..." DNA 7(2):99–106 (Mar. 1988).

Sorge, J. et al. "Complete Correction of the Enzymatic Defect of Type I..." Proc. Natl. Acad. Sci USA 84 pp. 906–909 (Feb. 1987).

Choudary S. et al, "The Molecular Biology of Gaucher Disease..." Cold Spring Harbor Symposia on Quantitative Biology vol. LI:1047–1052 (1986).

Maeda, S. "Production of Human α-Interferon in Silkworm..." Nature vol. 315:592–594 (Jun. 1985).

*Primary Examiner*—Robert A. Wax
*Assistant Examiner*—Rebecca Prouty
*Attorney, Agent, or Firm*—William G. Gosz

[57] ABSTRACT

Recombinant enzymatically active glucocerebrosidase is produced by a eukaryotic cell. Also, a cell includes nucleic acid encoding enzymatically active glucocerebrosidase; also a eukaryotic organism contains such a cell. Also, a method for producing enzymatically active glucocerebrosidase includes steps of introducing glucocerebrosidase-encoding nucleic acid into a eukaryotic cell, causing the cell to express glucocerebrosidase, and purifying the glucocerebrosidase from the cell.

6 Claims, 12 Drawing Sheets

Structure of a Glc$_3$Man$_9$GlcNAc$_2$ oligosaccharide schematic diagram of a Glc$_3$Man$_9$GlcNAc$_2$ oligosaccharide Man$_7$GlcNAc$_2$ Man$_9$GlcNAc$_2$ Man$_8$GlcNAc$_2$ Man$_3$GlcNAc$_2$ Man$_4$GlcNAc$_2$ Man$_4$GlcNAc$_2$ Man$_5$GlcNAc$_2$ Man$_6$GlcNAc$_2$ Man$_6$GlcNAc$_2$

FIG.2

CHANGE CCCACATGG TO CCACCATGG
BY OLIGO DIRECTED MUTAGENESIS

DELETE 3' 290 bp UNTRANSLATED SEQUENCE

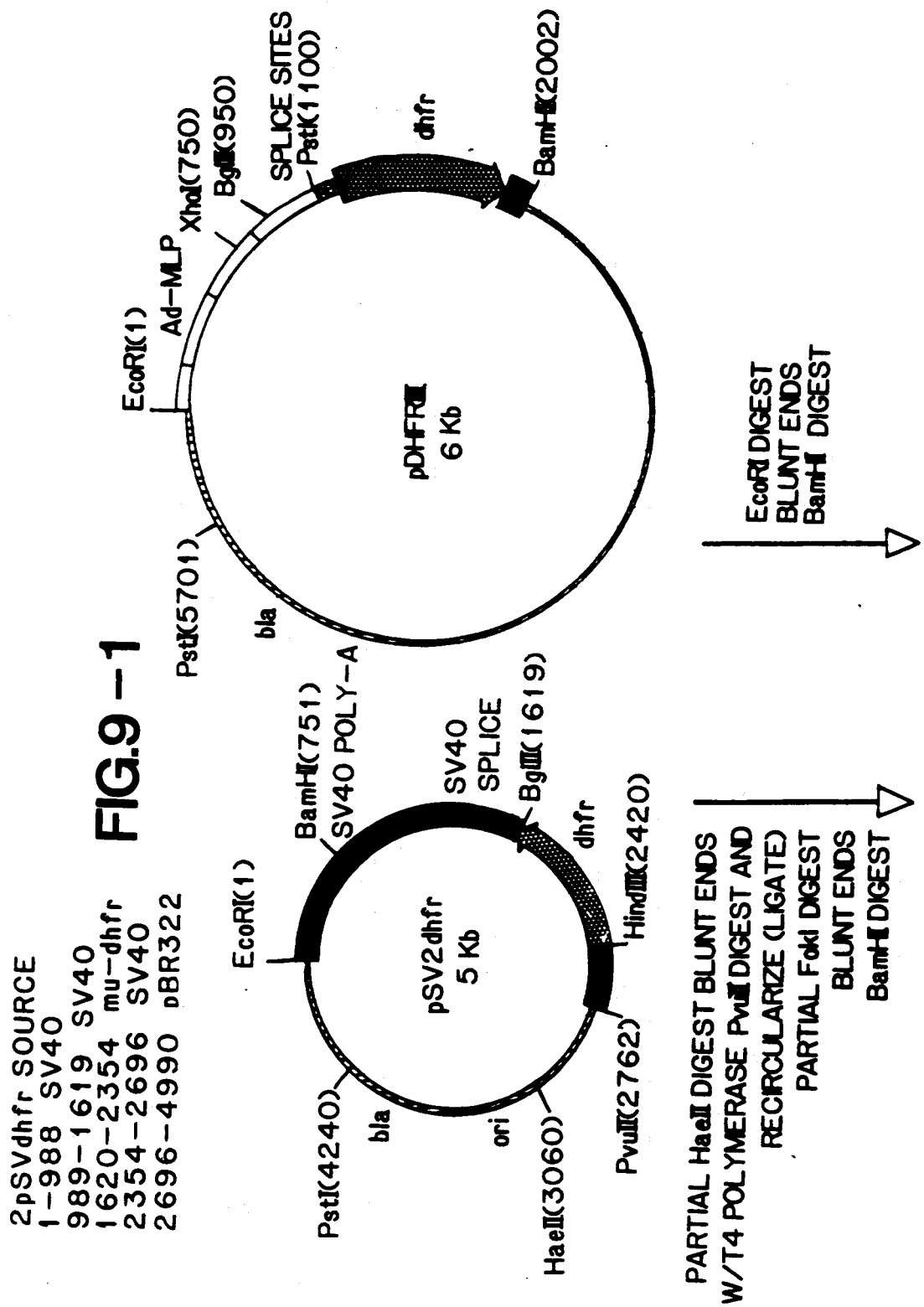

ENZYMATICALLY ACTIVE RECOMBINANT GLUCOCEREBROSIDASE

This is a division of co-pending application Ser. No. 07/455,507, filed on Dec. 22, 1989, now abandoned, which is a continuation-in-part of application Ser. No. 289,589, filed Dec. 23, 1988, now abandoned.

BACKGROUND OF THE INVENTION

This invention relates to expression of enzymatically active recombinant glucocerebrosidase.

Gaucher's disease is an autosomal recessive lysosomal storage disorder characterized by a deficiency in a lysosomal enzyme, glucocerebrosidase ("GCR"), which hydrolyzes the glycolipid glucocerebroside. In Gaucher's patients, deficiency in this enzyme causes the lycolipid glucocerebroside, which arises primarily from degradation of glucosphingolipids from membranes of white blood cells and senescent red blood cells, to accumulate in large quantities in lysosomes of phagocytic cells, mainly in the liver, spleen and bone marrow. Clinical manifestations of the disease include splenomegaly, hepatomegaly, skeletal disorders, thrombocytopenia and anemia.

Current treatments for patients suffering from this disease include administration of analgesics for relief of bone pain, blood and platelet transfusions, and in severe cases, splenectomy. Joint replacements may be necessary for patients who experience bone erosion. Brady, 1966, 275 New England Journal of Medicine 312, proposed enzyme replacement therapy with GCR as a treatment for Gaucher's disease. However, Furbish et al., 1978, 81 Biochem. Biophys. Research Communications 1047, observed that infused human placental GCR does not reach the site at which it is active, namely lysosomes of cells of the reticuloendothelial system, but rather is taken up by hepatocytes. Furbish et al., 1981, 673 Biochem. Biophys. Acta 425, improved delivery of human placental GCR to phagocytic cells by treating the GCR sequentially with neuraminidase, $\beta$-galactosidase and $\beta$-N-acetylhexosaminidase, and demonstrated that the treated GCR was taken up more efficiently by rat Kupffer cells than untreated protein.

Sorge et al., 1985, 82 Proc. Nat'l. Acad. Sci., USA 7289, and Tsuji et al., 1986, 261 J. Biol. Chem. 50 describe cloning and sequencing of a gene encoding human GCR.

SUMMARY OF THE INVENTION

In general, in one aspect, the invention features recombinant enzymatically active GCR produced by a eukaryotic cell. The term "recombinant GCR" ("rGCR") is used herein to mean any GCR produced from genetically manipulated GCR encoding nucleic acid inserted into a cell, such as, e.g., an insect cell, a yeast cell, or a mammalian cell such as, e.g., a CHO cell. The nucleic acid is generally placed within a vector, such as a plasmid or virus, as appropriate for the host cell; for expression in an insect cell, for example, the nucleic acid can be placed within an insect virus such as, e.g., a baculovirus. "Insect cell", as that term is used herein, means any living insect cell, such as, e.g., a Dipteran or Lepidopteran cell, present within a living insect or in tissue culture. "Mammalian cell", as that term is used herein, means any living mammalian cell, such as, e.g., a rodent cell, or a primate cell, present within a living mammal or in tissue culture. The term "enzymatically active" is used herein with respect to recombinant GCR to mean that the rGCR is able to hydrolyze a glucocerebroside, and can cleave the low molecular substrate 4-methyl-umbelliferyl-$\beta$-D-glucoside with an activity of at least $10^6$ units per milligram of rGCR.

In a second aspect, the invention features recombinant enzymatically active GCR having at least one exposed mannose residue, wherein the GCR is capable of specifically binding with a human mannose receptor protein.

The term "GCR having at least one exposed mannose residue" means that the GCR is glycosylated and at least one of the carbohydrate groups attached to the GCR has a carbohydrate chain terminating with a mannose residue. Preferably, the exposed mannose residue is readily available to bind with a mannose receptor protein, the exposed mannose residue being positioned external to the GCR in its three dimensional configuration. A GCR that is "capable of specifically binding with a human mannose receptor protein" as that term is used herein is a GCR that is specifically recognized by the receptor protein at an exposed mannose residue.

In preferred embodiments, the rGCR has an amino acid sequence with at least 95% homology to an amino acid sequence of a primate GCR, e.g., of a human GCR; the rGCR has at least two exposed mannose residues; the rGCR includes a carbohydrate moiety having between 3 and 9 mannose residues; preferably the mannose residues are arranged in a Man$_3$ to Man$_9$ structure (referred to as Man$_3$GlcNAc$_2$, etc.); the receptor protein naturally occurs in a phagocytic cell; and the GCR is produced within an insect cell such as, e.g., a Dipteran or a Lepidopteran cell, or within a yeast cell, or within a mammalian cell such as, e.g., a CHO cell.

FIG. 1 shows as examples a variety of carbohydrate moieties having between 3 and 9 mannose residues arranged in a Man$_3$ to Man$_9$ structure. The term "Man$_3$ to Man$_9$ structure", as used herein, refers to arrangements of mannose residues such as are shown in FIG. 1, and their structural isomers.

In a third aspect, the invention features a eukaryotic cell containing genetically manipulated nucleic acid, capable of expression in the cell, encoding enzymatically active rGCR capable of specifically binding with a human mannose receptor protein.

In preferred embodiments, the nucleic acid is a vector including DNA encoding an amino acid sequence having at least 95% homology to an amino acid sequence of a naturally occurring GCR; most preferably having 95% homology to an amino acid sequence of a naturally occurring primate GCR such as, e.g., a human GCR.

In other preferred embodiments, the nucleic acid is DNA lacking at least 50% of the region that is present in a naturally occurring GCR gene between the promoter of the GCR coding sequence and the ATG start site of the gene; more preferably the nucleic acid is the DNA present in the plasmid pVL941.GCRD21, or in the plasmid pAc373.GCR2.2; and the cell is an insect cell transformed with such plasmids.

In other preferred embodiments, the nucleic acid is DNA present in the plasmid pGB20, or in the plasmid pGB37, or in the plasmid pGB42; and the cell is a mammalian cell, preferably a Chinese hamster ovary cell, transformed with any of such plasmids or cotransformed with plasmid pGB34 and any of such plasmids.

In other preferred embodiments, the cell containing the GCR-encoding nucleic acid is an insect cell, a yeast cell, or a mammalian cell.

In a related aspect, the invention features a living insect including an insect cell containing the GCR-encoding nucleic acid, or a living mammal including a mammalian cell containing the GCR-encoding nucleic acid, as described above.

In another aspect, the invention features a method for producing enzymatically active rGCR, including steps of introducing rGCR-encoding nucleic acid into a eukaryotic cell, causing the cell to express the rGCR, and purifying the rGCR. Expressed rGCR that is retained by the cell can be purified from an extract of the cell; expressed rGCR that is secreted by the cell into the surrounding medium can be purified directly from the medium.

In preferred embodiments, the method includes culturing the cell in vitro, or growing the cell in vivo within a living eukaryotic organism, such as a living insect or mammal.

The invention provides enzymatically active rGCR in a form that is specifically recognized by human mannose receptor proteins. The rGCR of the invention is suitable for administration to a human suffering from Gaucher's disease using a standard enzyme replacement protocol. The invention also provides enzyme which is free from viral or bacterial agents commonly found in human tissues such as, for example, human placenta, from which GCR is conventionally derived. In addition, the rGCR of the invention is secreted in large amounts from the cells in which it is produced into the surrounding medium, from which it is readily purified.

Other features and advantages of the invention will be apparent from the following description of the preferred embodiments thereof, and from the claims.

DESCRIPTION OF THE PREFERRED EMBODIMENTS

The drawings will first briefly be described.

Drawings

FIG. 1 is a diagrammatic representation of various forms of mannose-terminating carbohydrate moiety of rGCR and of a typical complex-type carbohydrate moiety; circles represent mannose residues, black triangles represent glucose residues, black squares represent N-acetylglucosamine residues, open squares represent galactose residues, diamonds represent N-acetyl neuraminic acid residues, shaded triangles represent fucose;

Glucocerebrosidase (GCR)

As defined above, GCR has an enzyme activity which causes hydrolysis of a glucocerebroside. This invention includes all enzymes having such activity, a non-limiting example of which is the enzyme found within human placenta. A gene encoding this enzyme activity has been cloned as described above, and its DNA sequence is known. In the present application, applicants provide examples of use of this cloned DNA to cause production of rGCR having a structure suitable for therapeutic use in humans.

There follows a description of examples of insertion of human GCR-encoding DNA into insect vectors and of expression of the DNA by insect cells, and examples of insertion of human GCR-encoding DNA into mammalian vectors and expression of the DNA by mammalian cells. These examples are not limiting to this invention and those skilled in the art will recognize that applicants have enabled practice of this invention commensurate with the breadth of the appended claims.

GCR Expression in Insect Cells

Example 1

Insect Vector, pAc373.GCR2.2

In general, in order to insert a GCR gene within an insect virus, the gene is first inserted into a transfer vector, for example, pAc373, and then insect cells such as, for example, SF9 cells, are co-infected with the transfer vector together with wild-type viral DNA to allow recombination of the transfer vector and the viral DNA to produce a desired recombinant virus encoding GCR.

Figure 5:
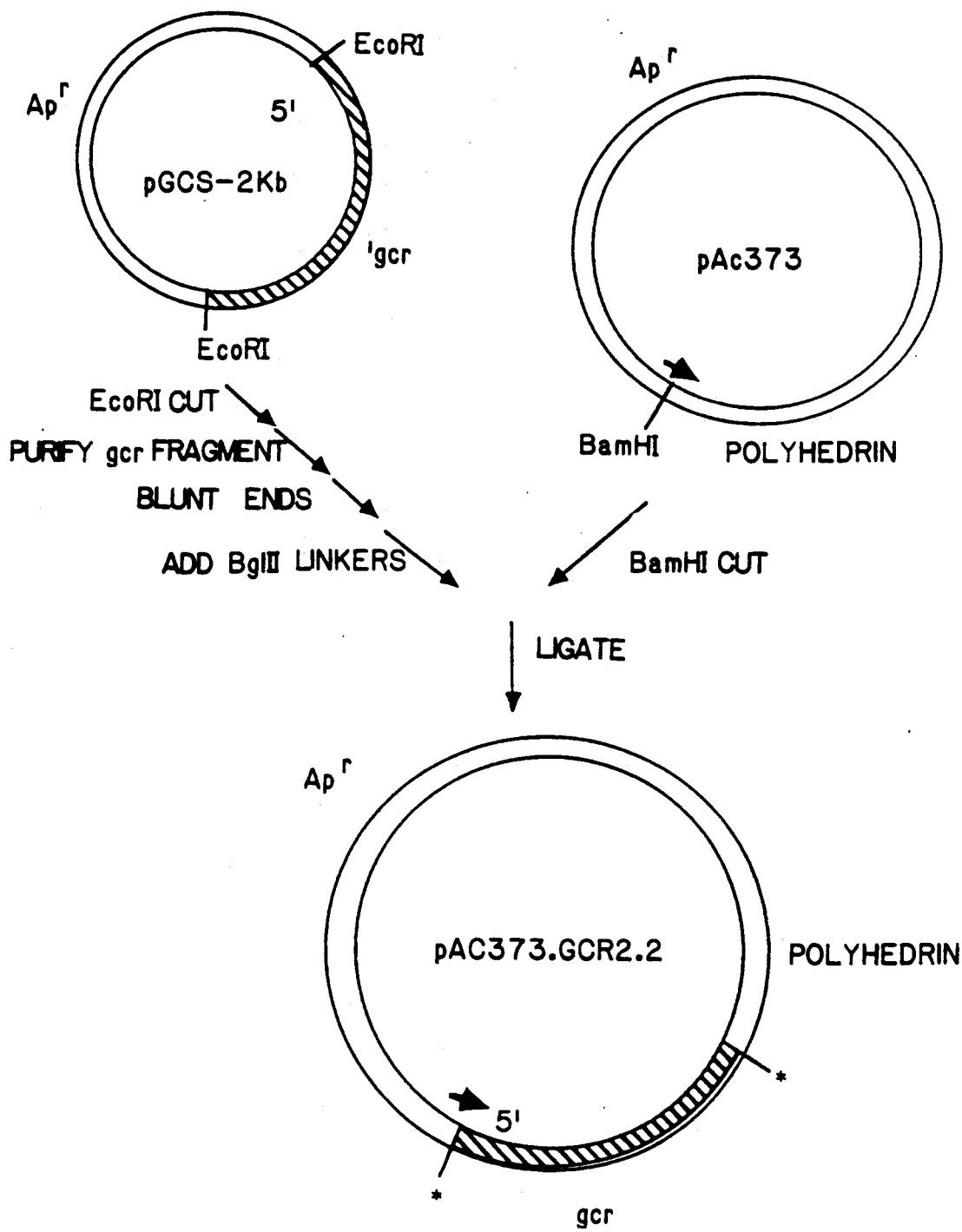
FIG. 5 is a schematic representation of construction of plasmid pAc373.GCR2.2.
Figures 2, 9:
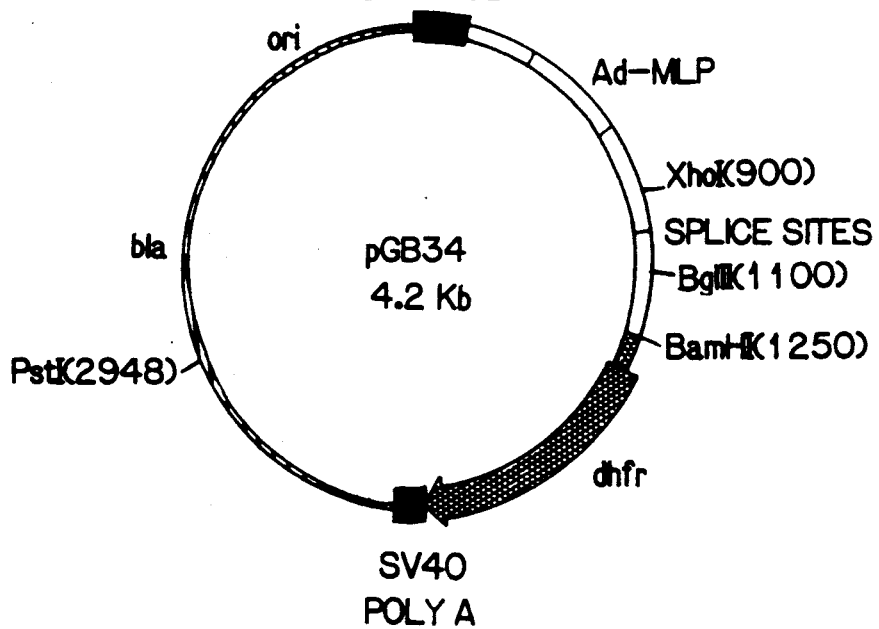
FIG. 2 is a schematic representation of the spatial relationships in various clones of the GCR gene among the GCR encoding regions, the 5' and the 3' noncoding regions and the polyhedrin regulatory sequences.
FIG. 9 is a schematic representation of construction of plasmids pGB37 and pGB42.
Figures 1, 10:
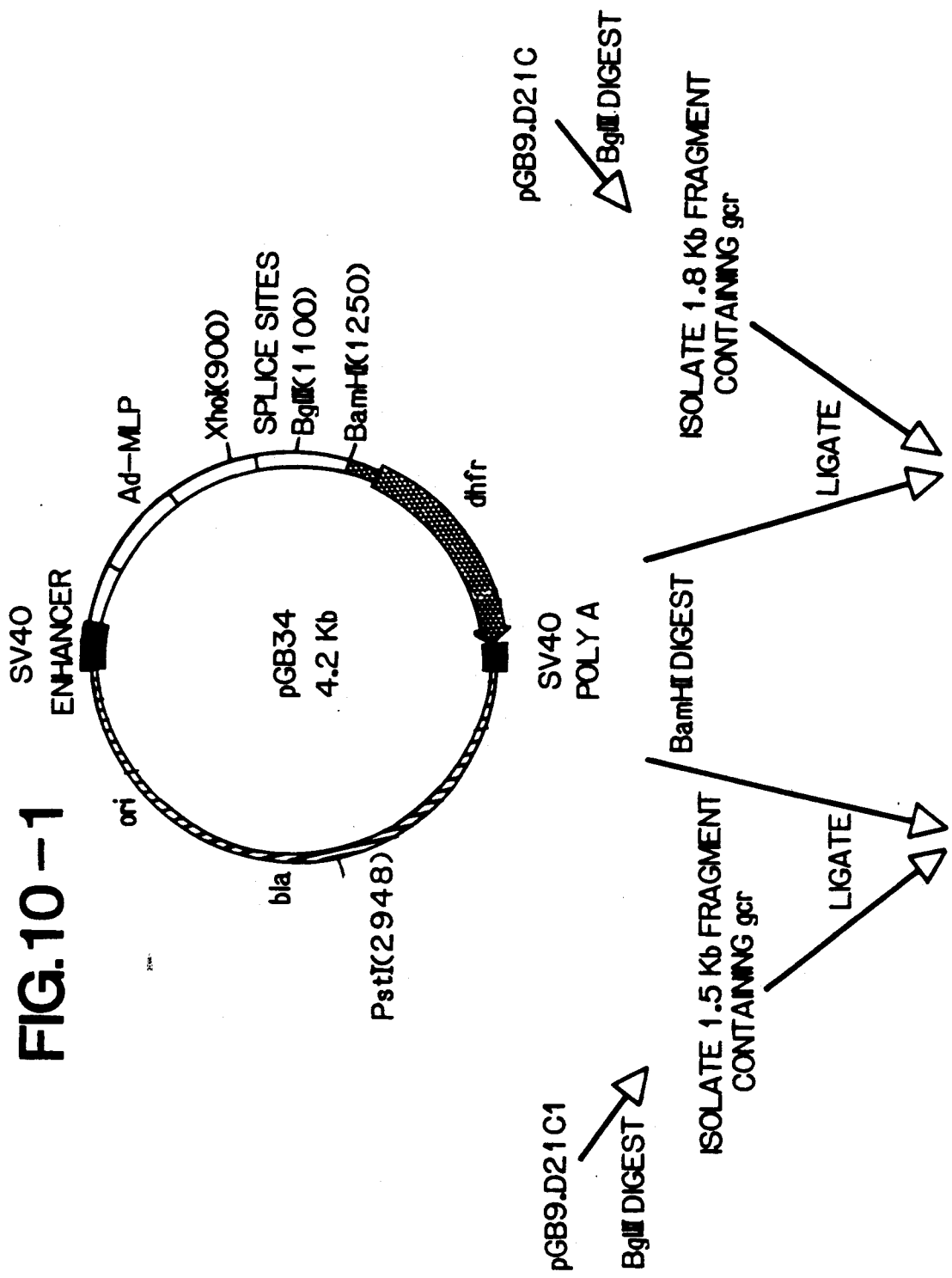
Figures 2, 10:
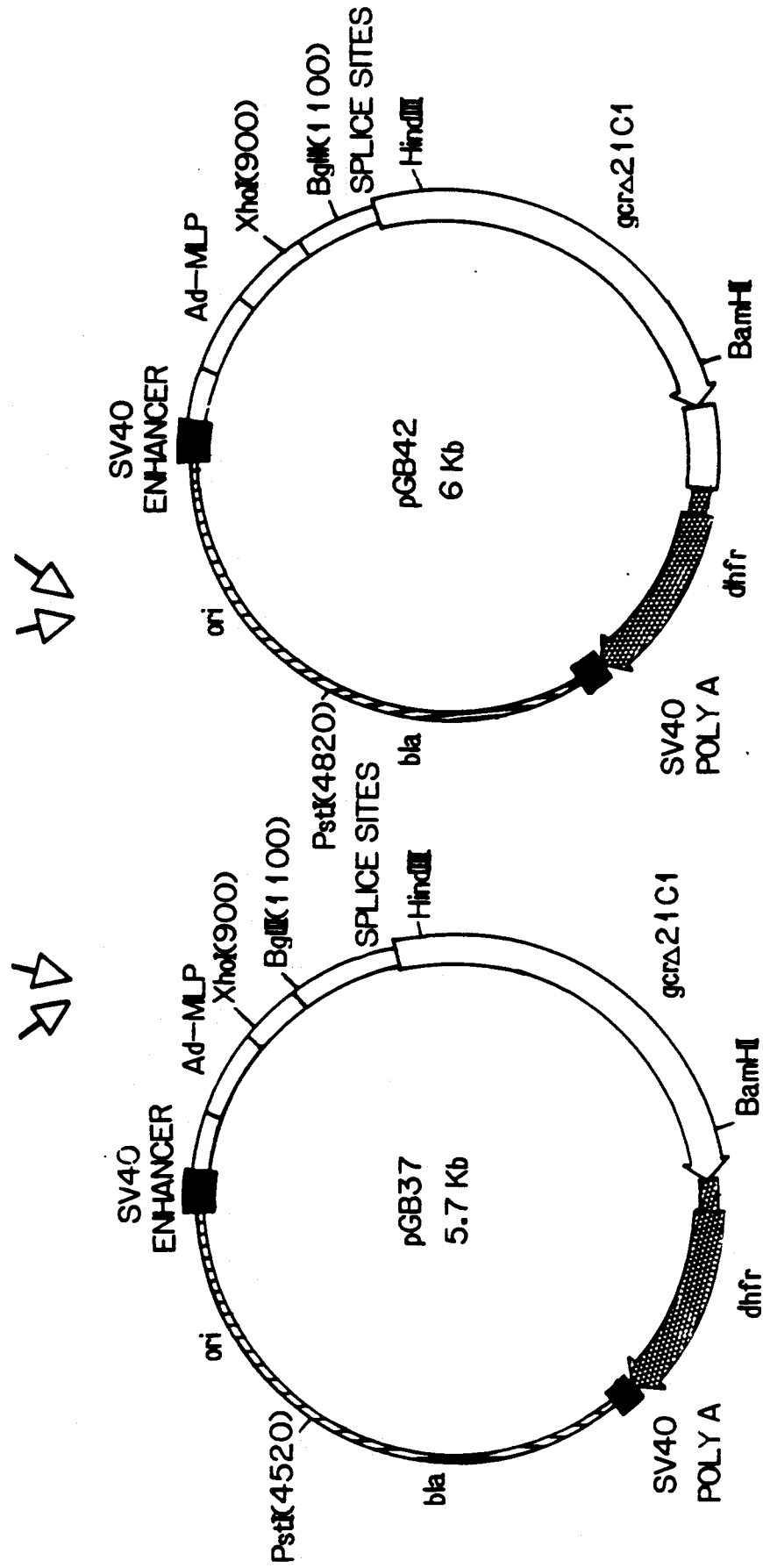

Referring to FIGS. 2 and 5, transfer vector pAc373 (obtained from Dr. M. Summers, Texas A & M University System, College Station, Tex.) has a BamHI cloning site to allow positioning of genes under the control of polyhedrin regulatory signals. Other promoters are also suitable in this invention, such as, e.g., the p10 promoter of Baculovirus. Plasmid pGCS-2Kb contains all of the coding sequence of GCR, including approximately 160 bp non-coding 5' and 500 bp noncoding 3' sequences, inserted into a unique EcoRI site of pBR322 (Sorge et al., 82 Proc. Natl. Acad. Sci. USA 7289, 1985). This plasmid was obtained from Dr. E. Beutler (Scripps Clinic and Research Foundation, LaJolla, Calif.) and the gene was cloned into pAc373 in the following manner. Plasmid pGCS-2Kb was cleaved with EcoRI and the ends blunt-ended with T4 polymerase. BglII linkers were added and the 2.2 kb GCR containing fragment was purified. The BglII ends are compatible with BamHI ends and allowed cloning into the BamHI site of pAc373. Recombinants containing the GCR gene in the correct orientation were identified by standard restriction analysis. The resulting plasmid was named pAc373.GCR2.2.

Transfer of the 2.2 kb fragment coding for GCR to the genome of the multiple nuclear polyhedrosis virus *Autographa californica* (AcMNPV) isolate E2 (obtained from Dr. M. Summers, Texas A & M University System, College Station, Tex.) was accomplished by co-transfecting the *Spodoptera frugiperda* cell line SF9 (a clonal isolate of *Spodoptera frugiperda* IPBL-Sf21-AE cells; American Type Culture Collection accession number CRL1711, obtained from Dr. M. Summers, Texas A & M University System, College Station, Tex.) with wild type virus DNA and pAc373.GCR2.2 prepared by standard procedures. Briefly, SF9 cells were cultured in TNM-FH medium (Hink, 266 Nature 466, 1970) containing 10% fetal calf serum at a temperature of 27° C.±1° C. Cells were cultured either in monolayer or in suspension. Cells were subcultured approximately 2-3 times a week. When grown in suspension, flask spinners were stirring at 50-60 rpm. The procedure for transfecting SF9 cells with viral DNA, or cotransfecting with a mixture of viral DNA and transfer vector DNA, was a modification of the calcium phosphate technique of Graham et al., 52 Virology 456, 1973, described by Burand et al., 101 Virology 286, 1980, and Carstens et al., 101 Virology 311, 1980. Briefly, a 25 cm² flask was seeded with $2 \times 10^6$ cells. After 1-2 hours the flask was aspirated, and 0.75 ml of Grace's medium containing 10% fetal calf serum was added to the adherent cells. 0.75 ml of 25 mM Hepes, pH 7.1, 140 mM NaCl, 125 mM CaCl$_2$, containing 1 ug of viral DNA (with or without 2 ug transfer vector DNA) was then added slowly. The flask was incubated for 4 hours at 27° C., after which the transfection mixture was removed and replaced with 5 ml of TNM-FH containing 10% fetal calf serum. For the production of the recombinant virus encoding the 2.2 kb GCR fragment from pGCS-2kb, $1 \times 10^6$ cells were plated in a 9 cm² dish, after which the cells were transfected with 2 ug of pAc373.GCR2.2 and 1 ug of *Autographa californica* closed covalent circular DNA ("cccDNA"). After cells are co-transfected with wild-type virus DNA and transfer vector DNA, a small percentage of the resulting transfectants produce recombinant virus, in which the polyhedrin gene is no longer expressed. These are identified by visually inspecting a sufficient number of viral plaques generated by infecting adherent cells with the supernatant harvested from the transfected flask 48 hours after the transfection. One hour after the infection with the transfection supernatant, an agarose overlay (1.5% low-melting SeaPlaque in growth medium) is applied. After 4-6 days, the plates are inverted and viewed under a dissecting microscope with low-angle incoming light, to discriminate wild-type from recombinant plaques. In this example, the same procedure was followed 4 days after transfection, and the medium was collected and serially diluted ($10^3$ to $10^5$). The serial dilutions (1 ml volume) were used to infect subconfluent cells ($5 \times 10^6$ in 100 mm dishes). After infection the cells were overlayed with low-melting agar. Six days post infection the plates were inspected for recombinant plaques.

Appropriate plaques were picked, subjected to two more rounds of plaque-purification, and used for the propagation of virus stock. A more detailed description of the plaque identification procedure is provided by Summers et al., A Manual of Methods for Baculovirus Vectors and Insect Cell Culture Procedures, Texas Agricultural Experiment Station Bulletin 1555 (1987).

Eight plaques having an appearance that suggested a lack of polyhedrin expression were selected and further plaque-purified. Virus from three plaques (designated 3-1-1, 3-2-1, 3-3-1) were further propagated and cells infected with these three isolates were analyzed for GCR expression.

The following assays were performed to ensure that sufficient rGCR having sufficient enzyme activity is produced by the selected clones. First, cell lysates of adherent cells which were separately infected with the three above described isolates were prepared and analyzed for the presence of GCR-specific DNA sequences. Cells were lysed in 0.5M NaOH, the lysate was neutralized with 10M NH$_4$Ac, and the solution was passed through nitrocellulose using a dot-blot apparatus (BioRad). The nitrocellulose sheet was processed according to standard DNA hybridization procedures, and probed with the 2.2 kb GCR fragment ($^{32}$P-labeled) from pGCS-2kb. Cells infected with viral isolates 3-2-1 and 3-3-1 contained GCR sequences, whereas cells infected with 3-1-1 and cells infected with wild-type virus did not. The structure of one such clone encoding a GCR-encoding sequence is shown in FIG. 2, where the GCR-encoding DNA is inserted within the partially deleted polyhedrin gene.

Two assays were employed for determination and quantification of the enzymatic activity of the recombinant human glucocerebrosidase. Three days after infection, the cells were lysed in 50 mM Na-phosphate pH 6.8/1% deoxycholate, and these lysates were used in the enzymatic assays. The first assay is based on the hydrolysis of the low molecular-weight substrate 4-methyl-umbelliferyl-β-glucoside (4MU-Glc). Although several other glucosidases are capable of cleaving this substrate and releasing the fluorescent aglycon, at low pH and in the presence of taurocholate (an inhibitor of several other non-specific glucosidases) this assay is useful for determining the level of expression of rGCR. This expression was compared with the level of 4MU-Glc activity in SF9 cells infected with wild type virus. The assay was performed at pH 5.9, in 100 mM potassium phosphate buffer containing 0.15% Triton X-100 and 0.125% taurocholate, essentially as described by Suzuki, 138 Meth. Enzymol. 749, 1987. rGCR having an activity of at least $10^6$ U/mg is useful in this invention.

For a glucocerebroside-specific assay [$^{14}$C]-glucocerebroside (Brady et al., 1965, 240 J. Biol. Chem. 39) was used. After incubation of the enzyme preparation with this radioactive substrate, the mixture was precipitated with 5% TCA. The amount of glucose ($^{14}$C-radioactivity) remaining in the supernatant provides a direct measure of glucocerebrosidase activity.

Lysates derived from cells infected with isolate 3-1-1 did not show any activity above background levels with the radioactive substrate, whereas the lysates from cells infected with 3-2-1 and 3-3-1 showed substantial activity.

An immunological assay was also used to determine the amount of GCR expressed by SF9 cells. Generally, this assay involved the following procedure. In a 24-well plate, cells were seeded at a density of $5 \times 10^5$ cells/well. Cells were infected at a multiplicity of infection of 10, and 3 days post-infection, the medium was harvested and cells lysed in buffer (10 mM Tris, pH 7.2, 150 mM NaCl, 5 mM EDTA, 10% DOC, 0.1Triton X-100, 0.1% SDS, and 0.02% NaN$_3$). GCR was immunoprecipitated using a polyclonal rabbit antibody, and the precipitated protein was subjected to SDS-PAGE. After electrophoresis, the protein was transferred to nitrocellulose, and the resulting western blot was probed with the same antibody. The amount of bound antibody was determined using biotinylated protein A and alkaline phosphatase conjugated streptavidin. By comparison with known quantities of human placenta-derived GCR, it was estimated that, for both active isolates, $10^6$ cells produced approximately 2–4 ug of rGCR.

Example 2

Insect Vector, pVL941.GCRD21

Figure 1:
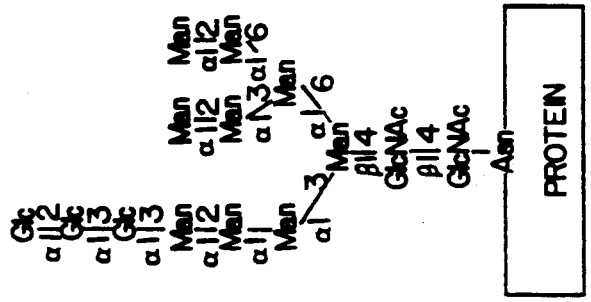
Figure 1:
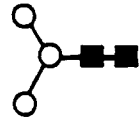
Figure 1:
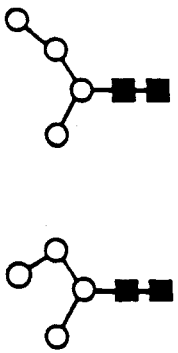
Figure 1:
Figure 1:
Figure 1:
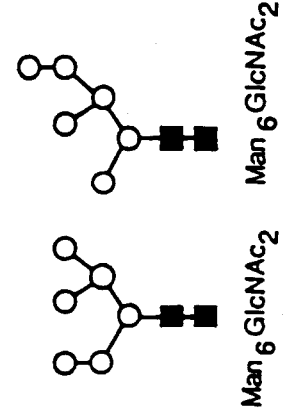
Figure 3:
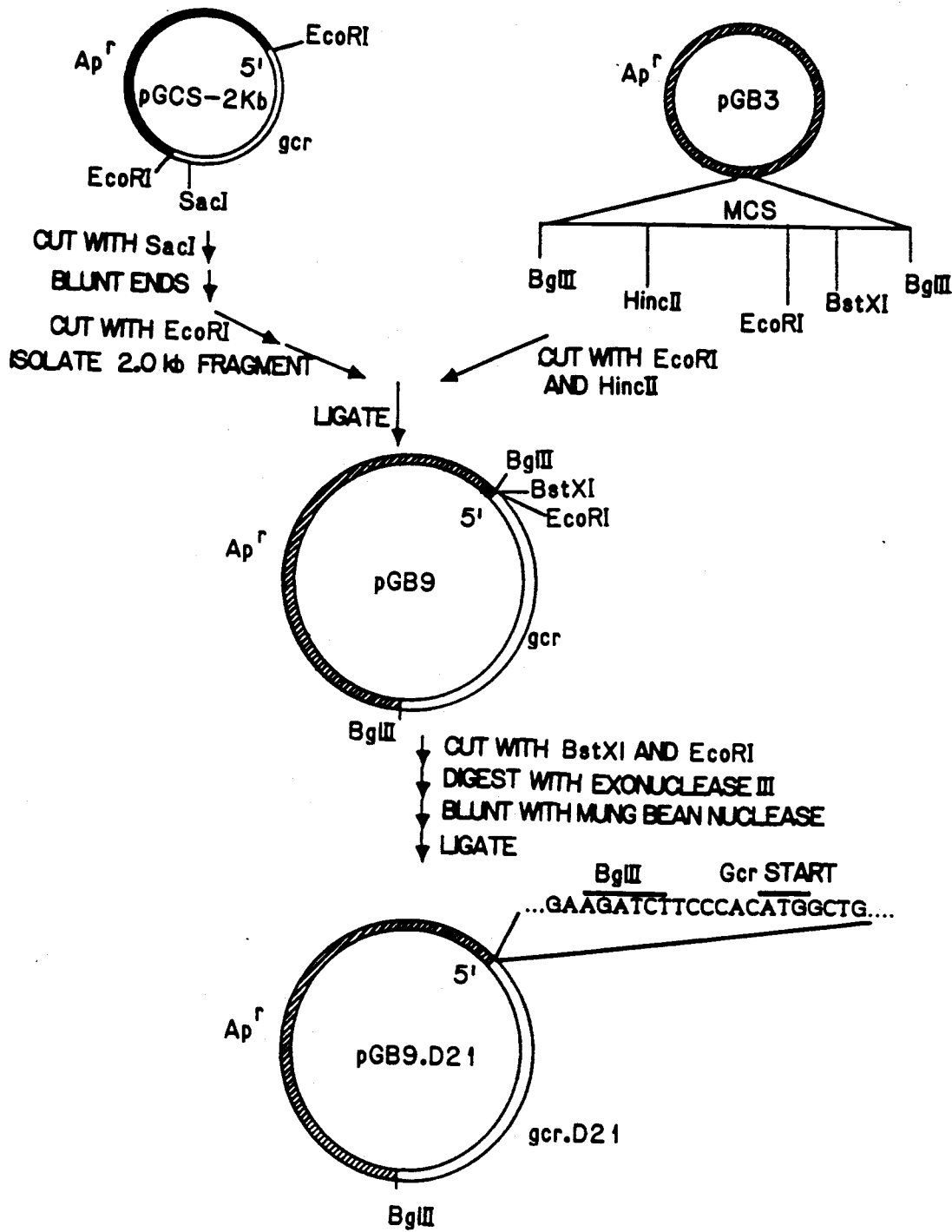
FIG. 3 is a schematic representation of construction of a deletion version of GCR (with a 5' noncoding region removed and a portion of the 3' noncoding region removed) inserted within a plasmid, namely plasmid pGB9.D21.

In order to optimize the expression of the GCR gene in insect cells, excess non coding sequence from the 5' and 3' ends of the gene were removed. The start codon for GCR should be placed as close to the polyhedrin gene regulatory sequences as possible in order to minimize sequence- or distance-associated negative effects on expression of GCR. This procedure minimizes or eliminates message destabilizing sequences at the 3' and 5' end of the GCR gene. To this end, referring to FIGS. 2, 3 and 4, we constructed the plasmid pGB9.D21 (FIG. 3), which carries a deletion derivative, GCR.D21, bounded by BglII sites. This BglII cassette carrying the GCR gene has 5 bases at the 5' end and 290 bases at the 3' end between the cloning (BglII) ends and the GCR coding sequences, compared to 160 and 500 bases, respectively, in the original cDNA pGCS-2kb with EcoRI cloning ends. The stepwise construction of pGB9.D21 is summarized in FIG. 3. Briefly, the GCR cDNA clone, pGCS-2kb, was cleaved approximately 290 base pairs from the 3' end of the GCR coding sequence with SacI and the ends blunt-ended with T4-DNA polymerase. A second cut, approximately 160 bp from the 5' end of GCR, with EcoRI created a 2.0 kb fragment containing the GCR coding sequence. This fragment was purified and ligated to HincII and EcoRI cut pGB3 to form pGB9. E. coli plasmid pGB3 was constructed from pBluescript SK+ (Stratagene, La Jolla, Calif.) by independently blunting the SacI and ApaI sites with T4 polymerase and ligating in BglII linkers. The resulting plasmid, pGB3, contains BglII linkers at either end of its multiple cloning site and retains lacZ activity in the host XL-1 Blue. pGB9 was digested with BstXI, EcoRI, and then with exonuclease III and mung bean nuclease to remove excess 5' non-coding sequence between the BglII site and the 5' end of the GCR coding sequence. After this treatment the ends were religated, and the plasmids were used to transform E. coli XL-1 blue. Transformants were screened using restriction analysis, and then DNA sequencing was used to determine the lengths of the deletions. Using this approach we identified pGB9.D21, which has only 5 bp between the BglII site and the start codon of GCR.

Figure 4:
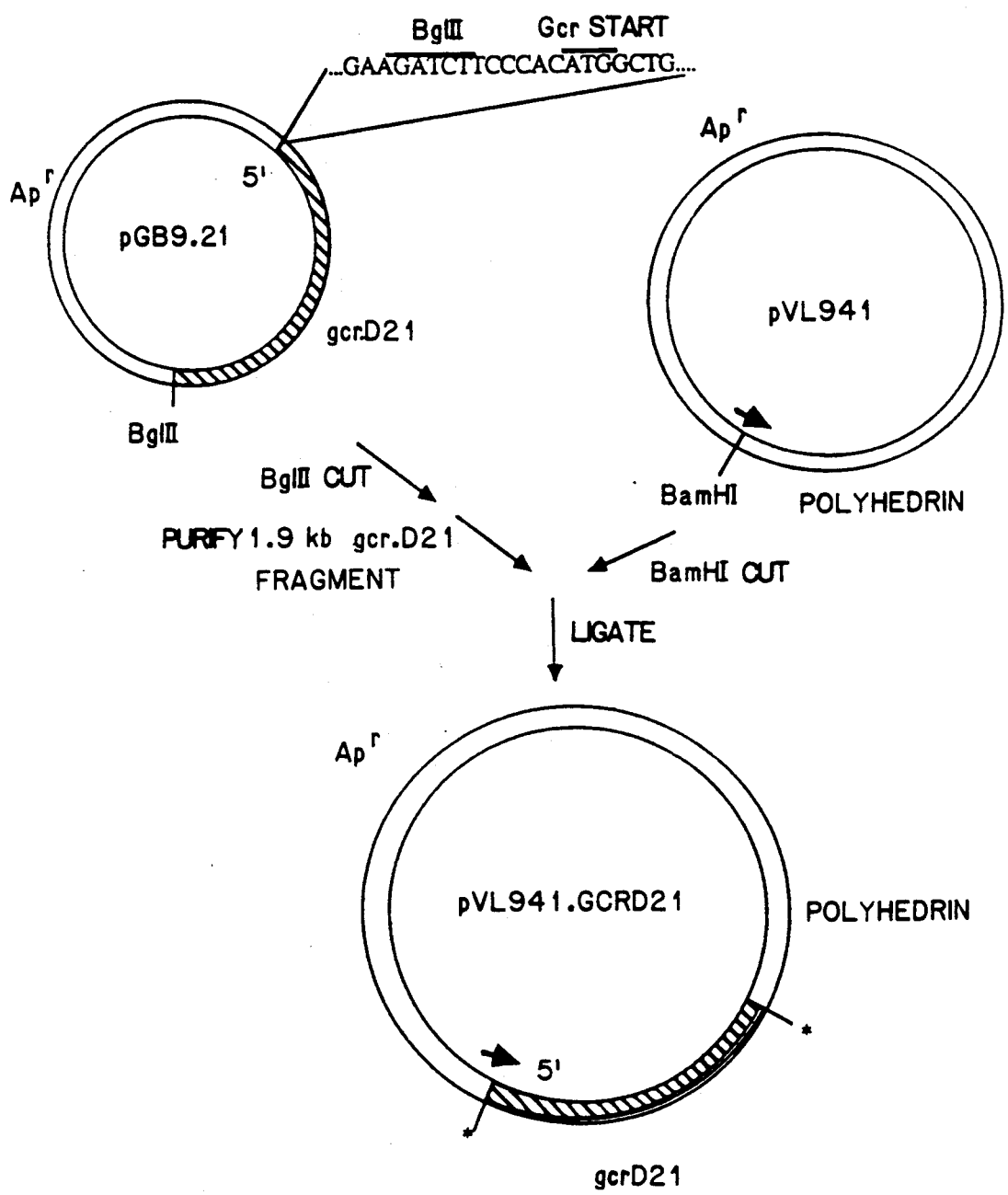
FIG. 4 is a schematic representation of construction of plasmid pVL941.GCRD21.

The shortened version of the GCR-encoding fragment, GCR.D21, was then cloned into a transfer vector, pVL941, as shown in FIG. 4. Transfer vector pVL941 (obtained from Dr. M. Summers, Texas A & M University System, College Station, Tex.) is very similar to pAc373, as it contains a BamHI cloning site for the positioning of genes under the control of the polyhedrin regulatory signals. The main difference between the two vectors is that the polyhedrin regulatory sequence of pAc373 extends only to position −8 relative to the polyhedrin translation start codon, whereas in pVL941 the entire 5' non coding regulatory sequence of the polyhedrin gene is present. This difference may result in an increase in the expression of genes placed under the control of the regulatory sequence.

Transfer of the GCR cDNA fragment spanning the −6 to +1850 domain (see FIG. 2) to the AcMNPV genome was accomplished by co transfecting SF9 cells with wild-type virus DNA and pVL941 GCRD21. The procedures followed for cotransfection and for subsequent isolation of a viral plaque resulting from a recombinant, non-polyhedrin coding virus, were as described above for pAc373.GCR2.2. Upon infection with this recombinant virus, cells produced material that cross-reacted with the polyclonal anti-GCR antibody, and that was enzymatically active as determined by the 4-MU-glucoside and [$^{14}$C]glucosylcerebroside assays.

Production of rGCR in insect cells

To produce rGCR in sufficient amount to be useful, uninfected insect cells are grown and then infected by standard procedure with one of the above recombinant viruses and the resulting protein is purified as follows. SF9 cells are grown either adherently or in suspension culture, in a spinner flask, e.g., a Bellco 500 ml flask operated at 50–60 rpm. The culture medium is, e.g., TNM FH (Hink, 266 Nature 466, 1970) supplemented with 10% fetal calf serum. The SF9 cells can be adapted to lower fetal calf serum concentrations, as described by Tramper et al., 469 Ann. N.Y. Acad. Sci. 279, 1986. Alternatively, it is possible to grow cells in serum-free medium, as described, e.g., by Roder, 69 Naturwissenschaffen 92, 1982; or to grow insect cells encapsulated in microcapsules to allow growth to high cell densities, and facilitate large scale insect cell culture, e.g., as described by King et al., 10 Biotechnology Letters 683, 1988.

Purification of rGCR produced in insect cells rGCR was purified from the culture medium of SF9 cells infected with recombinant virus as follows. Three days post infection the medium (containing the rGCR) was separated from the cells by centrifugation of the cell suspension (15 minutes, 2000 rpm in a Sorvall RC3). After centrifugation the medium was subjected to hydrophobic chromatography on a butyl substituted matrix e.g., TSK-gel, Toyopearl Butyl 650C (Nest Group, Southboro, Mass.). A column of 25 ml (1.6×12 cm) is sufficient for at least 500 ml of culture medium. The column was washed with 50 mM citrate buffer pH 5.0, containing 20% ethylene glycol, and fractions were eluted with an ethylene glycol gradient from 20 to 80%. The fractions were collected and assayed for GCR activity using the 4MU-glucoside assay described above. In a typical experiment, a recovery of 85% was obtained. The partially purified GCR was then subjected to a second hydrophobic chromatography step, on a phenyl-substituted matrix, e.g., TSK gel, Toyopearl Phenyl 650S (Nest Group, Southboro, Mass.). The GCR solution was brought to 50 mM citrate, pH 5.0, 20% ethylene glycol, and loaded onto a column equilibrated in the same buffer. Under these conditions the GCR adsorbed to the phenyl-substituted matrix. Subsequently, the column was washed with 50 mM citrate pH 5.0 to remove ethylene glycol. The GCR was then eluted with an ethanol gradient (in 50 mM citrate) from 0 to 50% and collected as described above. This procedure yielded a GCR preparation virtually free of other proteins. The resulting GCR was then subjected to oligosaccharide structural analysis, as described below.

Expression of GCR in Insects

To obtain expression of rGCR in whole insects the procedure of Maeda et al., 1985, 315 Nature 592, can be used. Briefly, a recombinant Bombyx mori nuclear polyhedrosis virus (BmNPV) is generated encoding rGCR. This recombinant virus, obtained as extracellular virus from cultured cells, is used to infect silkworm larvae by injection into the body cavity of the silkworms. The rGCR protein is recovered from the haemolymph. Alternatively, since BmNPV is a baculovirus similar to Autographa californica multiple nuclear polyhedrosis virus with respect to lifecycle, mode of replication, polyhedrin production and DNA homology, a similar procedure can be used with recombinant AcMNPV harboring a GCR gene. The recombinant virus harvested from infected cultured SF9 cells is used to infect permissive insects, such as larvae of Spodoptera frugiperda, or Trichoplusia ni by injection of the virus into the insect. The recombinant virus is allowed to replicate in the infected insect, which then produces rGCR in place of polyhedrin. After a suitable period, the recombinant protein is harvested from the insect.

In another method, the insect can be infected by orally administering virus encoding rGCR. The infectivity of AcMNPV depends on its target cell, as well as on the viral form. Nuclear polyhedrosis viruses occur in two forms, known as extracellular virus and occluded virus. The latter form is produced late in infection, and consists of multiple virus particles entrapped in polyhedra. Polyhedra are large, proteinaceous structures which are formed in the nucleus of the infected cell by the deposition of the major structural virus-encoded protein polyhedrin, thus embedding many virus particles. After cell or insect death these polyhedra remain infective when administered orally. The virus particles released in the midgut of an orally infected insect by hydrolysis of the embedding polyhedra are capable of infecting the midgut cells. Secondary infection of the other organs of the insect then follows. Polyhedra-embedded, occluded virus particles, mixed in the dietary intake, are an effective way of infecting large numbers of insects. A procedure for producing recombinant occluded virus is described by Emery et al., 1987, 1 protein Engineering 359. Briefly, a fragment encoding the polyhedrin promoter together with a GCR gene downstream of that promoter is cloned into a plasmid representing an AcMNPV DNA restriction fragment encoding polyhedrin and its promoter, and sufficient sequence 5' and 3' of the gene to allow recombination after co-transfection. The cloning site in this plasmid is upstream (but in the opposite orientation) of the natural polyhedrin promoter present in that plasmid. The resulting transfer vector has, therefore, both the normal polyhedrin gene and a GCR gene, each with its own copy of the polyhedrin transcriptional machinery. Co-transfections of Spodoptera frugiperda cells with this vector together with infectious, polyhedrin-negative AcMNPV DNA yields recombinant virus which encodes both polyhedrin and GCR. The two forms of this recombinant virus can thus be obtained. The occluded form is useful as described above for infecting insect larvae orally.

Expression In Mammalian Cells

Optimization Recombinant GCR Gene Cassette

Figure 6:
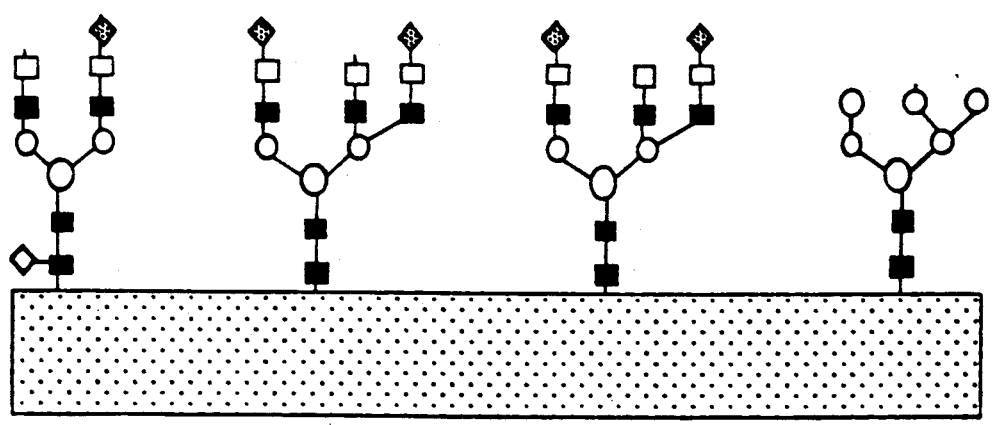
FIG. 6 is a schematic representation of construction of plasmids pGB9.D21C and pGB9.D21C1.

To optimize expression of GCR in mammalian cells, we further modified the GCR.D21 BglII cassette containing the gcr gene. In general, with reference to FIG. 6, the modifications were made using oligonucleotide directed mutagenesis (described generally in Kunkel, 1986, 82 Proc. Natl. Acad. Sci. U.S.A. 488-492; Wang et al., 1989, 7 Biotechniques, 1000-1010) to alter the nucleotide sequence near the GCR translation start to match the consensus sequence (CCACCATGG) for optimal translation in mammalian cells (as described in Kozak, 1986, 44 Cell 283-292); and to delete the excess sequence 3' of the gcr.D21C stop codon. The excess 3' sequence deletion removes potential message destabilizing sequences, and permits modulation of DHFR expression relative to GCR from bicistronic vectors.

Vector constructions

Figure 7:
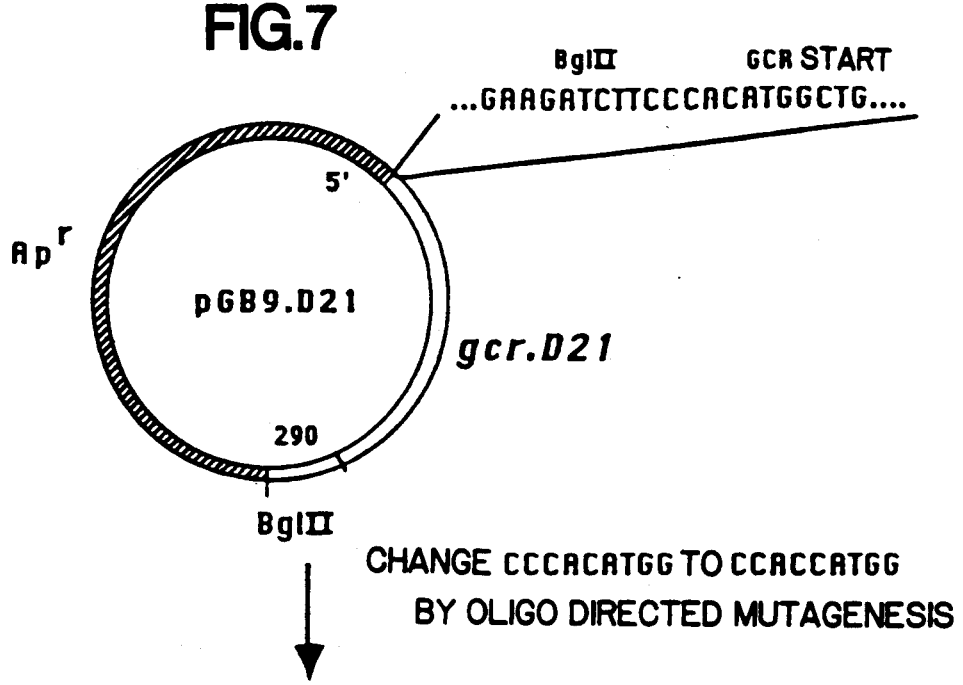
FIG. 7 is a schematic representation of construction of plasmid pGB20.
Figure 7:
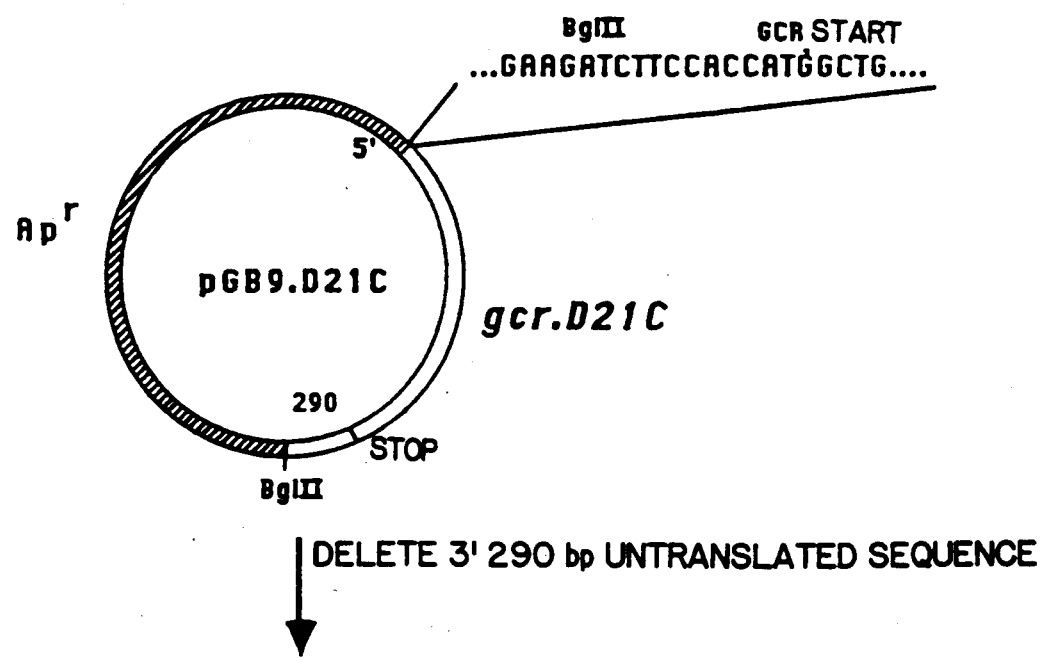
Figure 7:
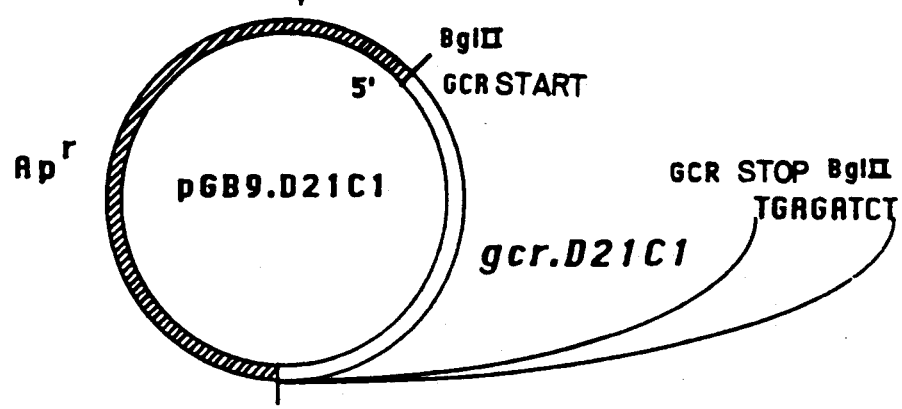

A bicistronic gcr-dhfr expression vector for CHO cells was constructed as shown in FIG. 7 from the vector pSV2-dhfr (described in Subramani et al., 1981, 9 Molecular and Cellular Biology 854-864). This vector, pGB20, contained gcr.D21C followed by dhfr under the control of the SV40 early promoter. DHFR expression depends upon ribosomes translating the dhfr after translating gcr, which is located adjacent at the 5' end of the dhfr message. This bicistronic arrangement reduced levels of expression of DHFR relative to GCR. A resulting gain in GCR expression relative to DHFR can be realized after stable transfectants have been selected using methotrexate.

A second series of bicistronic gcr expression vectors were constructed having the following characteristics: 1) transcription of gcr driven by a SV40 enhancer-Adenovirus major late promoter (Ad MLP) combination; 2) transcription of gcr in a bicistronic arrangement with dhfr; 3) termination and polyadenylation signals from SV40; and 4) a minimal 2 kb segment of DNA containing a prokaryotic origin and ampicillin resistance gene, but lacking the "poison" sequences which can be deleterious in mammalian cells (Lusky and Botchan, 1981, 293 Nature 79-81).

Figure 8:
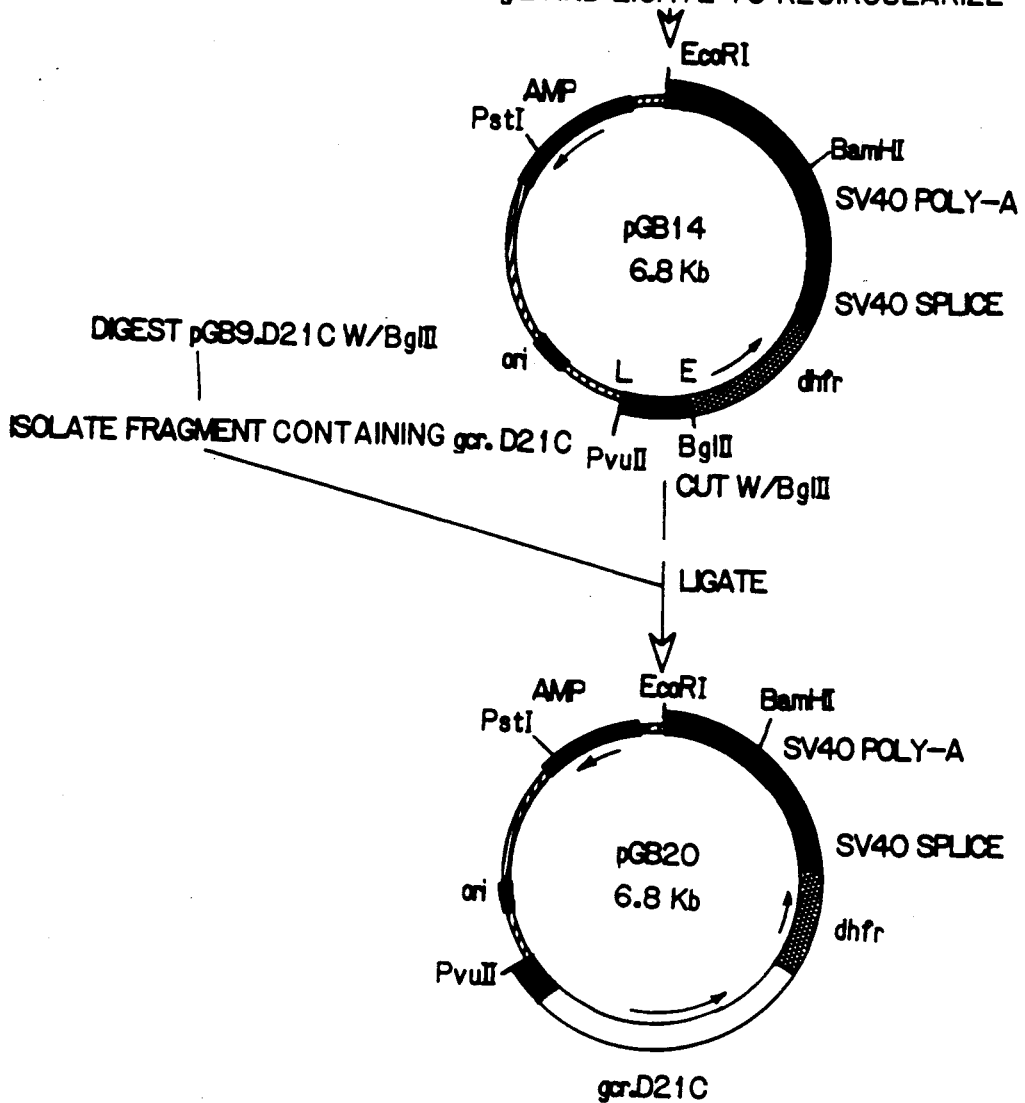
FIG. 8 is a schematic representation of construction of plasmid pGB34.

The base vector, pGB34 was constructed from pSV2dhfr as shown in FIG. 8. In a first step "poison" sequences between the PvuII and MaeII sites which might adversely affect expression in the final vector were removed. The resulting plasmid carries the SV40 enhancer (72 bp repeat), the pBR322 replication origin and the ampicillin resistance coding gene (bla) within a minimal fragment (2 kb) between the FokI and EcoRI sites. In a second step the 2 kb FokI-EcoRI fragment combined with a fragment from pDHFRIII (described in Berkner and Sharp, 1985, 13 Nucleic Acids Research 841-857) containing the Ad MLF and the dhfr gene and the SV40 polyadenylation signal. Excess sequence between the polyadenylation site and the pBR322 sequences were removed and the PstI cloning site was changed to BamHI by standard procedures using BamHI linkers. The resulting construct, pGB34, carries very little sequence in excess of that required for efficient production of recombinant proteins in mammalian cells. Versions of this vector were constructed using either gcr.D21C or gcr.D21C1 (shown in FIG. 6) for expression of GCR in CHO cells, as shown in FIG. 9. These constructs express DHFR at different levels, thus modulating DHFR selection and the relative amplification of GCR expression. These constructs can be used by themselves as bicistronic amplifiable gcr expression vectors; alternatively, the more widely used scheme of cotransfection using pGB34 can be used.

Transfecting Mammalian Cells

Any of several procedures can be used for introducing the vector DNA into mammalian cells, including calcium phosphate transfection and electroporation (described generally in F. M. Ausubel et al., eds., 1989, Current Protocols in Molecular Biology, pages 9.1.1–9.1.4 and 9.3.1–9.3.2, respectively, Wiley & Sons, N.Y.), Lipofectin TM transfection (as described by the manufacturer, Bethesda Research Laboratories, Gaithersburg, Md.), protoplast fusion (as described, e.g., in Sandri-Goldin et al., 1981, 1 Mol. Cell. Biol. 743-52, or polybrene transfection. Selection of recombinant colonies is performed by incubating the cells in culture medium devoid of ribonucleosides and deoxyribonucleosides, containing dialyzed fetal calf serum.

Amplifications

To increase expression of rGCR the cells can be subjected to an amplification procedure similar to the one described in F. M. Ausubel et al., eds., 1989, Current Protocols in Molecular Biology, pages 9.9.1–9.9.6, Wiley & Sons, N.Y.), which is similar to the procedure described in R. J. Kaufman et al., 1982, 159 J. Cell. Mol. Biol. 601-21. In general, higher levels of expression result from higher levels of methotrexate resistance. Other amplification procedures can be utilized as well, by using other amplifiable genes instead of the dhfr gene. Examples are the ornithine decarboxylase gene, the adenosine deaminase gene, and others, as well as combinations thereof, known to persons of ordinary skill. Examples have been reviewed by R. J. Kaufman in J. Setlow, Ed., 1989, 9 Genetic Engineering 155–198, Plenum Press, N.Y. In order to get amplification using other genes, the dhfr gene in the vectors described above is replaced by the gene of choice, e.g., the ornithine decarboxylase gene or the adenosine deaminase gene; after transfection with such a vector, amplification can be obtained using the appropriate selective medium.

Assays

Enzymatic activity of recombinant GCR expressed in chinese hamster ovary cells was measured using 4-methyl-umbelliferyl-B-D glucoside as a substrate. Enzymatic hydrolysis of this substrate generates a fluorescent product, which is quantitated using a spectrofluorometer. Details of this procedure are described in Methods of Enzymology, Vol. L, pp. 478-79, 1978. The assay is caried out under conditions in which other, non-GCR glucosidase activities are partially inhibited, i.e., by using a phosphate buffer, pH 5.9, 0.125% taurocholate, 0.15% Triton X-100.

Another way to establish the presence of recombinant GCR is by using a polyclonal antibody raised in rabbits against a preparation of glucocerebrosidase purified from human placenta. The medium or the cell lysate from GCR producing cells can be subjected to SDS-polyacrylamide gel electrophoresis, after which proteins are transferred from the gel to nitrocellulose. The presence of rGCR on nitrocellulose is established by probing with the antibody, which is detected by standard techniques using the biotinylated protein A-alkaline phosphatase conjugated streptavidin technique, or biotinylated goat-anti-rabbit IgG antibody-alkaline phosphatase-conjugated streptavidin, or any other standard method for detection of antibody on nitrocellulose. Details of such procedures have been described in, for example, E. Harlow and D. Lane, Eds., Antibodies, a Laboratory Manual, Cold Spring Harbor Laboratory, N.Y., 1988.

Another way of determining production of rGCR by CHO cells is by labeling the growing cells in vivo with [35S]methionine, and then harvesting the medium and lysing the cells, e.g., in a buffer containing 50 mM citrate pH 6.5, 1% sodium cholate, at intervals after labeling. The lysate and medium are then immunoprecipitated using the polyclonal antibody according to standard procedures. The polyclonal antibody can be used in various forms, such as, e.g., in the form of antiserum, or purified on protein A-agarose or protein G-agarose, or affinity-purified over a matrix onto which glucocerebrosidase has been immobilized. A higher purity of the antibody generally results in a lower background signal. Alternatively, a monoclonal antibody against GCR can be used. Examples of these detection procedures have been described in, for example, E. Harlow and D. Lane, Eds., Antibodies, a Laboratory Manual, Cold Spring Harbor Laboratory, N.Y., 1988.

These detection methods demonstrated expression of rGCR in CHO cells. In a typical run, cells that were transfected with one of the vectors described above, either using the dicistronic approach or the co-transfection procedure, expressed rGCR at levels between 1–10 mg/L, varying with cell density, culture conditions and cell support matrix. The rGCR is found both intracellularly and in the medium. The intracellular rGCR is sensitive to endoglucosaminidase H and to endoglucosaminidase F, indicating that the carbohydrate chains on the protein are most likely of the so-called high-mannose type, and thus the intracellular rGCR is particularly useful for treatment of Gaucher's disease, as described below. The rGCR recovered from the medium is larger in molecular weight, and is resistant to endoglucosaminidase H.

Carbohydrate Structure of rGCR

To determine whether a rGCR produced as described above has been correctly glycosylated to be useful for treatment of Gaucher's disease the following procedure can be performed to determine the carbohydrate structure, and in particular the mannose configuration within the carbohydrate structure, of the rGCR. Generally, the carbohydrate should contain at least one exposed mannose and preferably has a $Man_3$–$Man_9$ structure, or a structure with the same functional features as a carbohydrate having a $Man_3$–$Man_9$ structure (e.g., other sugar residues can be substituted for one or more of the sugar residues shown). There are generally four oligosaccharide moieties in human placental GCR. Recombinant GCR having these moieties present in a $Man_3$–$Man_9$ structure has greater affinity than unglycosylated GCR for the mannose receptor in humans. The more mannose residues per oligosaccharide moiety, and the more such moieties, the greater this affinity. Recombinant GCR according to this invention has at least one such oligosaccharide with at least one exposed mannose, but preferably has two, three, or four such oligosaccharides each with a $Man_3$–$Man_9$ structure.

Analysis of oligosaccharides derived from rGCR generally followed the procedure described by Hirani et al., 162 Anal. Biochem. 485, 1987. Asn-linked oligosaccharides were released from SDS-denatured rGCR (100 ug) by incubation with N-glycanase enzyme (80 units) at 37° C. for 18 hours. The completeness of the reaction was judged by SDS-polyacrylamide gel electrophoresis. The liberated oligosaccharides were recovered in the supernatant after precipitating the protein with ethanol (75% v/v) and radiolabeled at the reducing end by treatment with sodium borotritide. Labeled oligosaccharides were analyzed by a combination of high performance liquid chromatography (hplc) and exoglycosidase digestion.

The degree of sialylation was determined by analyzing the tritium-labeled oligosaccharides by hplc on a Micropak AX-10 column pre-equilibrated in 25 mM $KH_2PO_4$, titrated to pH 4.0 with phosphoric acid. GCR with high sialic acid content is unlikely to useful in this invention, but GCR with a low sialic acid content, i.e., uncharged GCR, is more likely to have exposed mannose moieties. The column was eluted with the same buffer for 15 minutes and then for 30minutes using a linear gradient of 25 mM $KH_2PO_4$, pH 4.0, to a final concentration of 500 mM $KH_2PO_4$, pH 4.0. In this elution protocol, oligosaccharides eluted from the column in characteristic positions depending upon the number of attached sialic acid residues. The Asn linked oligosaccharides derived from recombinant GCR consisted primarily (95%) of neutral species. Such neutral species are potentially useful in this invention.

The size of each neutral and/or desialylated oligosaccharide was analyzed by hplc using a Micropak AX-5 column. The column was pre-equilibrated with acetonitrile:water (65:35) and elution was performed using a 60 minute gradient in which the water content of the solvent increased at the rate of 0.5%/minute. This procedure fractionates oligosaccharides according to size. The column was calibrated with oligosaccharide standards having the structures shown below. Analysis of the oligosaccharides derived from rGCR obtained from infected SF9 cells showed that they consisted of a single species with a retention time similar to $Man_3GlcNAc(Fuc)GlcNAc_{OT}$.

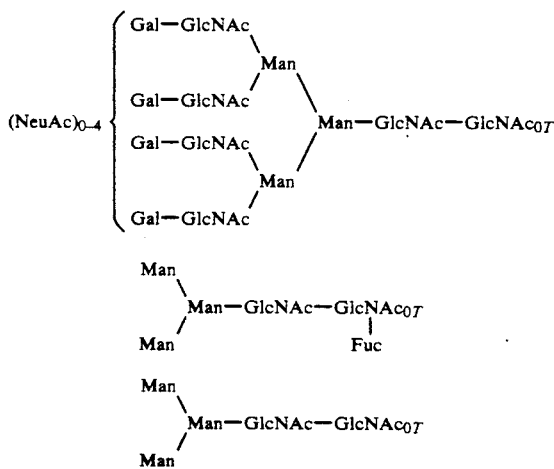

A presence of exposed mannose groups is readily determined by treatment of these oligosaccharides with mannosidases which specifically remove mannose groups. Such treatment, and the analysis of the results, is performed by standard procedures.

In another method for determining the usefulness of an rGCR, the ability of the rGCR to bind to and be taken up by macrophages is measured. This targeting of rGCR to macrophages is mediated by the Man/GlcNAc receptor and can be determined using thioglycollate-elicited peritoneal macrophages obtained from mice, as described by Stahl et al., 93 J. Cell Biol. 49, 1982. Briefly, mice (25–30 g, C57 strain) are injected intraperitoneally with 1–1.5 ml thioglycollate broth (Difco, Detroit, Mich.). After 3–4 days the mice are sacrificed by suffocation in $CO_2$ and the peritoneal cavity rinsed with phosphate buffered saline. The cells are pelleted by centrifugation (500 g, 10 min), resuspended in DME (GIBCO, Grand Island, N.Y.) containing 10% fetal calf serum, and plated in 96-well tissue culture plates. After 90 min. non-adherent cells are washed away, and the adherent macrophages are incubated for specified time periods, ranging from 0 to 180 minutes in culture medium containing specified quantities of rGCR, ranging from 0 to 20 ug in 200 ul at a temperature of 37° C., in the absence and presence of yeast mannan (2–10 mg/ml). After incubation, the medium containing excess rGCR is removed, the cells are washed several times and then lysed, and the amount of rGCR taken up by the cells is determined in the cell lysate. The amount taken up in the presence of yeast mannan is non-specific uptake. The difference between the two values is the amount taken up specifically via the Man/GlcNAc receptor. No uptake occurs when the experiment is done at 4° C., but the rGCR binds to the cell surface. In this way, Man/GlcNAc receptor-specific binding of rGCR can be determined.

Use

The rGCR of this invention is useful for therapeutic treatment of Gaucher's disease by providing a therapeutic amount of the rGCR. By therapeutic amount is meant an amount of rGCR which will cause significant alleviation of clinical symptoms of Gaucher's disease. Such rGCR must be post-translationally modified, as described above, to provide a carbohydrate structure which will target to human mannose receptors. Generally, such rGCR has at least two carbohydrate moieties each having a $Man_3$–$Man_9$ structure, and such rGCR represents at least 50% of the rGCR provided in the therapeutic composition. For example, provision of between 10 and 500 milligrams per 70 kg patient per month to provide that patient with between 0.25 and 3 grams rGCR over a one year period. The rGCR is provided in the form of a pharmaceutical composition in any standard pharmaceutically acceptable carrier, such as physiological saline, and is administered by any standard procedure, for example by intraveneous injection.

Deposit

An E. coli strain (DH5α) harboring the plasmid pVL941.GCRD21 was deposited on Dec. 22, 1988 with the American Type Culture Collection and was assigned ATCC accession number 67,866. An E. coli strain (DH5 alpha/pGB42) harboring the plasmid pGB42 was deposited on Dec. 21, 1989 with the American Type Culture Collection and was assigned ATCC accession number 68194.

Applicants and their assignee, Genzyme Corporation, acknowledge their responsibility to replace these cultures should they die before the end of the term of a patent issued hereon, 5 years after the last request for a culture, or 30 years, whichever is the longer, and their responsibility to notify the depository of the issuance of such a patent, at which time the deposit will be made irrevocably available to the public. Until that time the deposit will be made available to the Commissioner of Patents under the terms of 37 C.F.R. §1–14 and 35 U.S.C. §112.

Other Embodiments

Other embodiments are within the following claims. For example, rGCR having an appropriate carbohydrate structure can be produced by introducing GCR-encoding DNA into any vertebrate or invertebrate eukaryotic cell, and treating that cell during its growth with inhibitors of carbohydrate processing such as deoxy-mannojirimycin, swainsonine, castanospermine, deoxy-nojirimycin, N-methyl-deoxy-nojiricin, or their equivalent inhibitors. These inhibitors act to inhibit specific steps in the conversion of $Glc_3Man_9GlcNac_2$ to smaller species shown in the figure, thus, providing a greater number of exposed mannose residues.

We claim:

1. A method for producing enzymatically active glucocerebrosidase comprising the steps of:
   introducing nucleic acid encoding human glucocerebrosidase into a CHO cell;
   causing said cell to express and secrete said glucocerebrosidase into a culture medium; and
   purifying said glucocerebrosidase from said culture medium.

2. The method of claim 1 wherein the pH of said culture medium is between about pH 6.5 and pH 7.2.

3. The method of claim 2 wherein the pH of said culture medium is between about pH 6.6 and pH 6.8.

4. The method of claim 1 wherein said culture medium contains $O_2$ in an amount below about 50% saturation and sufficient to maintain the cells.

5. The method of claim 1 wherein said culture medium contains $O_2$ in an amount between about 20% saturation and about 30% saturation.

6. A method for producing enzymatically active glucocerebrosidase comprising the steps of:
   introducing a plasmid containing nucleic acid encoding glucocerebrosidase into a CHO cell, said plasmid being selected from the group consisting of pGB20, pGB37 and pGB42;
   causing said cell to express and secrete said glucocerebrosidase into a culture medium; and
   purifying said glucocerebrosidase from said culture medium.

* * * * *